(12) United States Patent
Dotterl et al.

(10) Patent No.: US 9,193,814 B1
(45) Date of Patent: Nov. 24, 2015

(54) HETEROGENEOUS SUPPORTS FOR HOMOGENEOUS CATALYSTS

(71) Applicants: Matthias Dotterl, Selbitz (DE); Helmut Alt, Bayreuth (DE); Roland Schmidt, Bartlesville, OK (US)

(72) Inventors: Matthias Dotterl, Selbitz (DE); Helmut Alt, Bayreuth (DE); Roland Schmidt, Bartlesville, OK (US)

(73) Assignee: Phillips 66 Company, Houston, TX (US)

( * ) Notice: Subject to any disclaimer, the term of this patent is extended or adjusted under 35 U.S.C. 154(b) by 0 days.

(21) Appl. No.: 14/797,338

(22) Filed: Jul. 13, 2015

Related U.S. Application Data

(62) Division of application No. 13/150,700, filed on Jun. 1, 2011, now Pat. No. 9,115,226.

(60) Provisional application No. 61/362,102, filed on Jul. 7, 2010.

(51) Int. Cl.
   *C07C 2/24* (2006.01)
   *C08F 136/06* (2006.01)
   *C08F 8/42* (2006.01)

(52) U.S. Cl.
   CPC .................. *C08F 136/06* (2013.01)

(58) Field of Classification Search
   None
   See application file for complete search history.

(56) References Cited

U.S. PATENT DOCUMENTS

| | | | |
|---|---|---|---|
| 3,832,418 A | 8/1974 | Bercik et al. | |
| 4,182,811 A | 1/1980 | Bocharov et al. | |
| 5,304,615 A | 4/1994 | Ambler et al. | |
| 5,731,101 A | 3/1998 | Sherif et al. | |
| 5,733,834 A * | 3/1998 | Soga | C08F 10/00 502/117 |
| 5,811,379 A | 9/1998 | Rossi et al. | |
| 6,063,725 A | 5/2000 | Sunaga et al. | |
| 6,291,733 B1 | 9/2001 | Small et al. | |
| 6,518,473 B2 | 2/2003 | Miller et al. | |
| 6,706,936 B2 | 3/2004 | O'Rear et al. | |
| 6,969,693 B2 | 11/2005 | Sauvage et al. | |
| 7,223,893 B2 | 5/2007 | Small et al. | |
| 7,351,780 B2 | 4/2008 | Hope et al. | |

OTHER PUBLICATIONS

Jun. 3, 2014 Office Action mailed in U.S. Appl. No. 13/150,700, filed Jun. 1, 2011.
Jun. 11, 2014 Amendment and Response to Office Action Mailed on Jun. 3, 2014 in U.S. Appl. No. 13/150,700, filed Jun. 1, 2011.
Jul. 16, 2014 Office Action mailed in U.S. Appl. No. 13/150,700, filed Jun. 1, 2011.
Aug. 26, 2014 Amendment and Response to Office Action Mailed on Jul. 16, 2014 in U.S. Appl. No. 13/150,700, filed Jun. 1, 2011.
Sep. 25, 2014 Office Action mailed in U.S. Appl. No. 13/150,700, filed Jun. 1, 2011.
Oct. 10, 2014 Response to Office Action Mailed on Sep. 25, 2014 in U.S. Appl. No. 13/150,700, filed Jun. 1, 2011.
Oct. 23, 2014 Office Action mailed in U.S. Appl. No. 13/150,700, filed Jun. 1, 2011.
Jan. 8, 2015 Amendment and Response to Office Action Mailed on Oct. 23, 2014 in U.S. Appl. No. 13/150,700, filed Jun. 1, 2011.
Feb. 11, 2015 Final Office Action issued in U.S. Appl. No. 13/150,700, filed Jun. 1, 2011.
May 4, 2015 Amendment and Response to Final Office Action Mailed on Feb. 11, 2015; and Request for Continued Examination in U.S. Appl. No. 13/150,700, filed Jun. 1, 2011.
May 28, 2015 Notice of Allowance/Allowability issued in U.S. Appl. No. 13/150,700, filed Jun. 1, 2011.

* cited by examiner

*Primary Examiner* — Yun Qian
(74) *Attorney, Agent, or Firm* — Gardere Wynne Sewell LLP; Chris P. Perque; Teresa J. Lechner-Fish

(57) ABSTRACT

A method of making a heterogenously supported catalyst useful in dimerization, oligomerization or polymerization is provided in which a catalyst precursor containing a metal and an aromatic group are alkylated onto an oligomeric support having at least one terminal unsaturated group by Friedel Crafts alkylation.

15 Claims, 4 Drawing Sheets

FIGURE 3

SIGNAL 1: FID1 A,

| PEAK NUMBER | RET TIME [min] | TYPE | WIDTH [min] | AREA [pA*s] | HEIGHT [pA] | AREA % | |
|---|---|---|---|---|---|---|---|
| 1 | 5.652 | MM | 0.2020 | 1.26952e5 | 1.04766e4 | 76.46249 | $C_6$ |
| 2 | 14.714 | MM | 1.3298 | 2.86035e4 | 358.48947 | 17.22773 | $C_9$ |
| 3 | 30.168 | MM | 0.5552 | 6296.33594 | 189.01099 | 3.79225 | $C_{12}$ |
| 4 | 32.395 | MM | 0.6095 | 2141.84961 | 58.56480 | 1.29002 | $C_{15}$ |
| 5 | 33.859 | MM | 0.5630 | 1188.70020 | 35.19019 | 0.71595 | |
| 6 | 35.164 | MM | 0.5164 | 560.04913 | 18.07458 | 0.33731 | |
| 7 | 36.500 | MM | 0.6631 | 289.31192 | 7.27152 | 0.17425 | |

TOTALS:                                              1.66032e5    1.11432e4

HETEROGENEOUS SUPPORTS FOR HOMOGENEOUS CATALYSTS

PRIOR RELATED APPLICATIONS

This application is a divisional of U.S. patent application Ser. No. 13/150,700, filed on Jun. 1, 2011, now is U.S. Pat. No. 9,115,226 B2, which claims the benefit of U.S. Provisional Application Ser. No. 61/362,102, filed on Jul. 7, 2010 and incorporated herein by reference.

FIELD OF THE INVENTION

The invention relates to methods of supporting catalysts for use in dimerization, oligomerization and polymerization reactions.

BACKGROUND OF THE INVENTION

Dimerization of olefins is well known and industrially useful. In particular, dimerization of 2-methylpropene to produce 2,4,4-trimethylpentene, commonly called isooctane, is a well known and useful reaction because the product can be used for gasoline reformulation. Branched saturated hydrocarbons, such as isooctane, have a high octane number, low volatility and do not contain sulfur or aromatics, and are, therefore, particularly useful for improving gasoline and making it more environmentally friendly. Dimerization of linear olefins also represents an attractive route for the production of high octane number blending components. The branched species, however, may also contribute to engine deposits. Thus, in some instances the lower octane number of products of dimerization of linear olefins may be offset by lower engine deposits.

Branched saturated hydrocarbons can be produced in different ways, e.g. by alkylation of olefins with isoparaffins and by dimerization of light olefins, in some instances followed by hydrogenation. Alkylation of 2-methylpropene (isobutene) with isobutane directly produces isooctane, and the dimerization reaction of 2-methylpropene produces 2,4,4-trimethyl-1-pentene and 2,4,4-trimethyl-2-pentene, amongst other products.

Use of ionic liquids for dimerization and/or oligomerization of olefins is well known, including for example, the processes disclosed in U.S. Pat. Nos. 5,304,615; 5,731,101; 6,706,936; 6,518,473 and 7,351,780, the disclosures of which are incorporated herein by reference.

Ionic liquids make an ideal solvent because they have very low volatility, and do not evaporate or burn very easily, resulting in safer processes. Also, the low melting point and negligible vapor pressure lead to a wide liquid range often exceeding 100 degrees C. (unlike the hundred degree Celsius range limit found for liquid water). Another advantage is that chemical and physical properties of ionic liquids can be "tuned" by selecting different anion and cation combinations, and different ionic liquids can be mixed together to make binary or ternary ionic liquids. It is even possible to have ionic liquid solvents that also function as catalysts or co-catalysts in reactions.

Perhaps the most important benefit of using ionic liquids in various reactions is simplified separation of the products. Most ionic liquids are polar, and hence non-polar products—like isooctane and octane—are immiscible therein. The biphasic process allows separation of the products by decantation and reuse of the catalysts. Further, the fact that the product is not miscible in the solvent, also tends to drive the reaction.

It is known that catalysts may be either heterogeneous or homogeneous catalysts. Homogeneous catalysts act by reacting within a single phase, and the catalyst is not supported. While a reaction involving a homogenous catalyst may result in a narrow weight distribution of products, it may be unfavorable because it can be difficult to separate the product from the reactants.

Heterogenous catalysts act by reacting at the boundary of two phases (such as a solid-liquid phase). While heterogeneous catalysts may be less selective than homogenous catalysts, they are advantageous in that the products are easier to separate and can offer a continuous manufacturing process. It would be advantageous therefore, to have a catalyst that provides the separability of a heterogenous catalyst with the ease of synthesis that can be achieved with ionic liquids.

It would be desirable, therefore, to utilize ionic liquids to attach oligomerization catalysts onto a solid support, thus providing an oligomerization catalyst system and reaction process useful in fixed bed reactors and which is readily used in a refinery environment.

SUMMARY OF THE INVENTION

One aspect of the invention provides a method of making a supported catalyst useful in reactions of addition monomers comprising: (a) contacting a catalyst precursor comprising at least one aromatic group and at least one active catalytic metal with a support material comprising at least one terminal unsaturated group in the presence of a Lewis acid by Friedel Crafts alkylation to form a supported catalyst precursor; and (b) contacting the supported catalyst precursor with a co-catalyst to form a supported catalyst.

In some embodiments, the support is one or more oligomers. In alternative embodiments, the support is one or more homo-, inter- or hetero-polymers. In yet other embodiments, the support is a mixture of oligomers and polymers.

In certain embodiments, the at least one terminal unsaturated group is at least one terminal vinyl group.

In some embodiments of the invention, the at least one active catalytic metal is selected from the Group 3-10 metals.

In certain embodiments of the inventive method, the support is polybutadiene having about 10 mol % terminal vinyl groups.

Some embodiments of the invention utilize an ionic liquid as the Lewis acid. In various embodiments, the inventive method employs ionic liquids consisting of an organic halide salt, such as an ammonium, phosphonium, or sulfonium salt, and a metal halide salt of aluminium, gallium, boron, iron (III), titanium, zirconium or hafnium.

In some embodiments of the invention, the co-catalyst is one or more alkylaluminum compounds. In particular embodiments, the co-catalyst is methylaluminoxane, ethylaluminum dichloride, triethylaluminum, diethylaluminum chloride, tri-isobutylaluminum, or a mixture of any thereof.

Another aspect of the invention provides a method for producing supported catalysts that are useful in dimerization, oligomerization or polymerization of addition monomers.

Another aspect of the invention provides supported catalysts produced according to the inventive method.

Yet another aspect of the invention provides a process for producing dimers from an addition monomer comprising contacting an addition monomer with the supported catalyst produced according to the inventive method.

DESCRIPTION OF THE FIGURES

FIG. 3 is a table containing the FID-GC analysis of the product of Example 1.

DESCRIPTION OF EMBODIMENTS OF THE INVENTION

Figure 1:
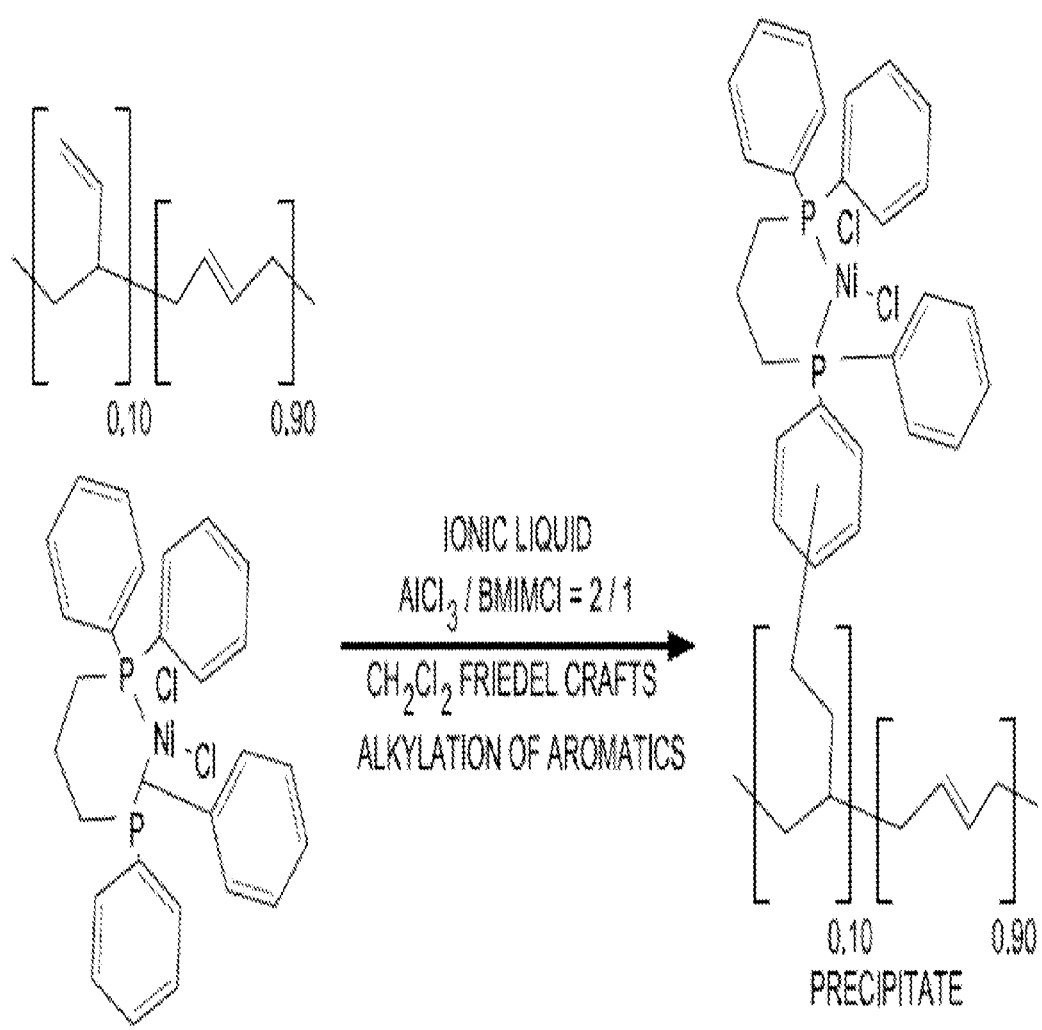
FIG. 1 illustrates the reaction mechanism for bonding a catalyst precursor onto a support wherein the support is polybutadiene and the catalyst precursor is diphenylphosphinopropane nickel dichloride to form a supported catalyst precursor.

Embodiments of the invention provide a method of producing a supported catalyst precursor for use in dimerization and/or oligomerization reactions. In some embodiments, the supported catalyst precursor may be activated, i.e., contacted with one or more activators or co-catalysts, in the presence of an olefin in a dimerization or oligomerization reactor. In alternative embodiments, the supported catalyst precursor may be activated prior to introduction into a dimerization or oligomerization reactor containing an olefin.

In some embodiments of the invention the catalyst precursor is supported on a support selected from the group of linear and branched oligomers having a molecular weight of between 500 and 500,000 and having at least one terminal unsaturated group, such as a vinyl group.

In alternative embodiments, the support is selected from linear and branched homo-, inter-, and hetero-polymers wherein the polymer includes at least one terminal unsaturated group.

In some embodiments of the invention, the support is polybutadiene, including e.g., 1,2 and 1,4 polybutadienes.

In preferred embodiments of the invention, the oligomeric or polymeric support does not include any heteroatoms, such as sulfur, oxygen or nitrogen. In yet other preferred embodiments of the invention, the oligomeric or polymeric support does not include aromatic groups.

Catalyst precursors useful in embodiments of the invention include any one or more catalyst precursors for use in dimerization or oligomerization reactions and containing one or more metals and one or more substituted and/or unsubstituted aromatic groups. While polymerization may occur using embodiments of the invention, in preferred embodiments the catalyst and co-catalyst are optimized for the dimerization reaction.

In specific embodiments, the catalyst precursor is especially useful in olefin dimerization reactions. Examples of such catalyst precursors are disclosed in U.S. Pat. Nos. 7,223,893, 6,518,473, and 6,291,733, the disclosures of which are incorporated herein by reference.

In some embodiments of the invention, the co-catalyst (i.e., activator) may be one or more of known such compounds useful in activating dimerization, oligomerization and/or polymerization catalysts, including for example, methylaluminoxane, ethylaluminum dichloride, and triethylaluminum. Examples of such cocatalysts are disclosed in U.S. Pat. Nos. 7,223,893, 6,518,473, and 6,291,733, the disclosures of which are incorporated herein by reference.

The catalyst precursor is attached to the support in preferred embodiments by Friedel-Crafts alkylation. Friedel-Crafts reactions are possible with any carbocationic intermediate such as those derived from alkenes and a protic acid, Lewis acid, enones, and epoxides.

In alternative embodiments of the invention, the aromatic component of a catalyst precursor may be alkylated onto a heterogenous support. In such embodiments, the complexation of an active metal may be conducted after the alkylation to form a supported catalyst precursor. The supported catalyst precursor may then be activated as described herein to form a supported catalyst composition.

Another aspect of the invention provides supported catalysts useful in dimerization, oligomerization or polymerization reactions.

As used herein the following terms and abbreviations have the meanings specified.

| | |
|---|---|
| $AlCl_3$ | aluminum trichloride. |
| BMIMCl or C4MIMCl | 1-butyl-3-methylimidazolium chloride |
| $EtAlCl_2$ | ethylaluminum dichloride |
| FID | Flame Ionization Detector |
| GC | Gas Chromatography |
| IL | ionic liquid |
| $Ni(dppe)Cl_2$ | diphenylphosphine-ethane nickel dichloride |
| $Ni(dppp)Cl_2$ | diphenylphosphine-propane nickel dichloride |
| $Ni(PPh_3)_2Cl_2$ | bis(triphenylphosphine) nickel dichloride |
| NMR | nuclear magnetic resonance |

A "catalyst precursor" is a transition metal compound or transition metal complex, which when activated by contact with a co-catalyst, is useful for dimerization, oligomerization or polymerization of additional polymerizable monomers.

"IL" or "ionic liquid" as used herein means a Lewis acidic ionic liquid consisting of an organic halide salt, such as an ammonium, phosphonium, or sulfonium salt, and a metal halide salt of aluminium, gallium, boron, iron (III), titanium, zirconium or hafnium.

The following example is illustrative only and should not serve to unduly limit the scope of the invention.

EXAMPLE 1

0.38 g of polybutadiene was dissolved in 30 ml methylene chloride at ambient atmospheric pressure. The polybutadiene had an approximate molecular weight of about 110,000 with 89-90 mol % 1,4-linkage and 10-11 mol % 1,2-linkage of the butadiene monomers. The term 10-11 mol % 1,2-linkage means there are 10-11 mol % pending vinyl groups in the chain, with the remaining double bonds being within the backbone (1,4-linkage).

0.40 g of $Ni(dppp)Cl_2$ was added to the polybutadiene solution. 1.5 ml of the Lewis acidic ionic liquid BMIMCl: $AlCl_3$ in a 2:1 ratio was slowly added to the polybutadiene: $Ni(dppp)Cl_2$ solution with stirring. Gelation was observed, indicating the formation of the supported catalyst precursor within several minutes and producing a gel. FIG. 1 illustrates this reaction in which the catalyst precursor is attached to the polybutadiene support by Friedel Crafts alkylation.

The gel was transferred into a filtration funnel and washed with acetone. Residual acetone in the gel was removed by high vacuum drying, leaving 0.59 g of powder product, the supported heterogenous catalyst precursor.

Figure 2:
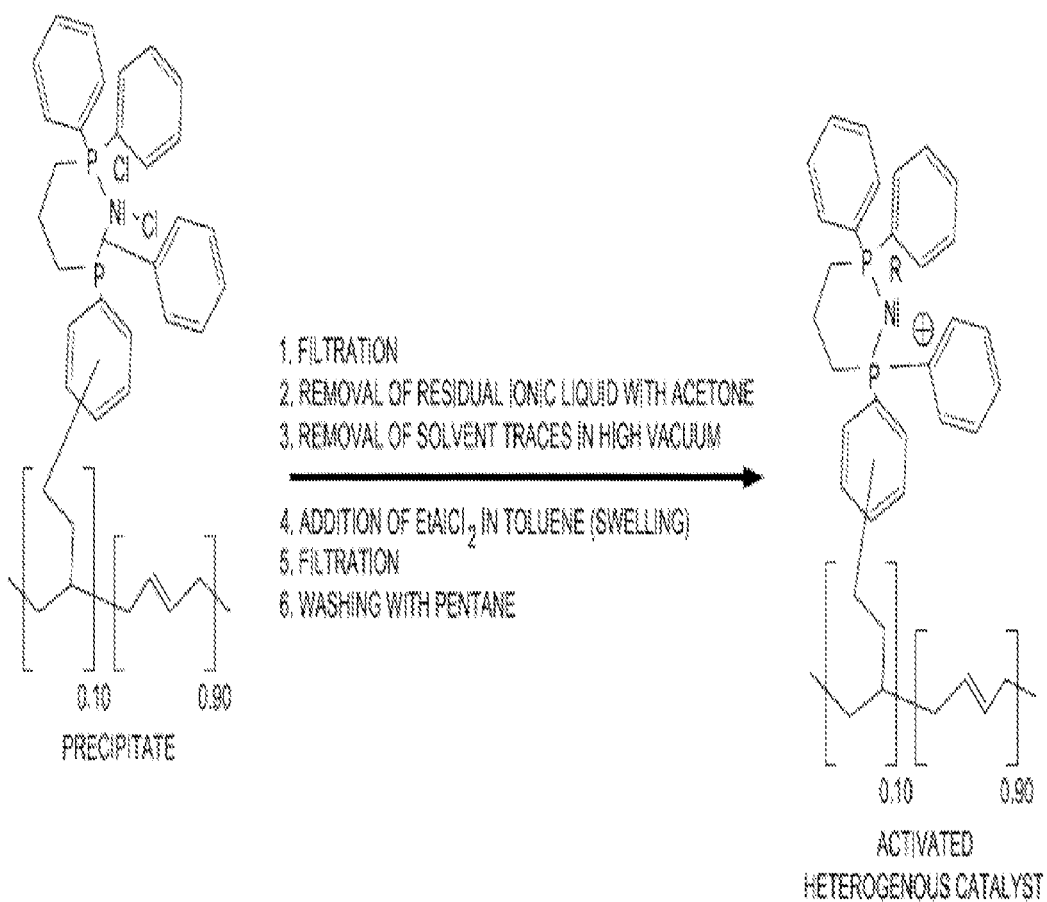
FIG. 2 illustrates the reaction mechanism of activating the supported catalyst precursor with co-catalyst/activator to form an activated supported catalyst.

$EtAlCl_2$ in toluene was used as the co-catalyst/activator in this example. 30 ml of 1.8 molar $EtAlCl_2$ in toluene was added to the powder product and the mixture was placed in an ultrasonic bath. This activation reaction, in which the supported catalyst is formed by contact of the supported catalyst precursor with cocatalyst, is illustrated in FIG. 2.

The powder product swelled and the remaining, unabsorbed $EtAlCl_2$ solution was removed by filtration. The swelled powder product, activated heterogenous catalyst, was washed three times with n-pentane and then stored under n-pentane.

Figure 4:
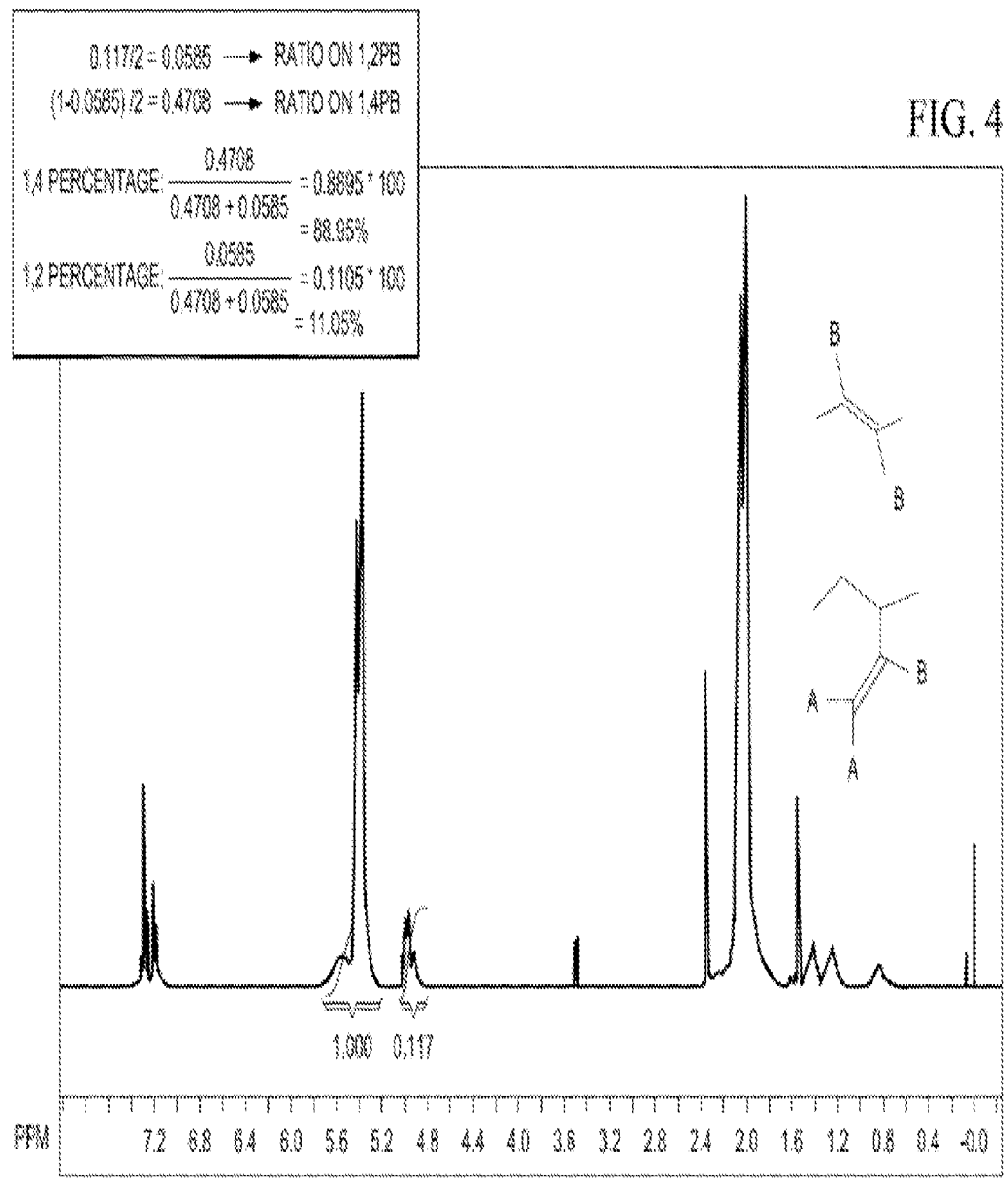
FIG. 4 is an NMR trace of the polybutadiene of Example 1 before the alkylation step, showing that the polybutadiene possessed around 10% 1,2 linkages.

Then the resulting supported catalysts was tested to confirm its catalytic activity. 6 ml of the activated heterogenous catalyst suspension (which equaled 0.08 g polymer) and 50 ml liquid propene were combined and placed in an ambient temperature waterbath and stirred for 195 minutes. After releasing the pressure, 22.99 g of product remained. Gas Chromatograph (GC) analysis of the product revealed propene dimer and propene trimer content of 76.5 wt % and 17.2 wt %, respectively. See FIGS. 3-4. Thus, the novel supported catalyst was functional and highly selective, resulting in more than 75% dimer formation. Thus, the new catalyst has high with all of the conveniences of a supported catalyst, especially advantages in recycling the catalyst.

While various embodiments in accordance with the disclosed principles have been described above, it should be understood that they have been presented by way of example only, and are not limiting. Thus, the breadth and scope of the invention(s) should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

The following patents are incorporated by reference herein in their entirety.

U.S. Pat. No. 5,304,615
U.S. Pat. No. 5,731,101
U.S. Pat. No. 6,291,733
U.S. Pat. No. 6,518,473
U.S. Pat. No. 6,518,473
U.S. Pat. No. 6,706,936
U.S. Pat. No. 7,223,893
U.S. Pat. No. 7,351,780

What is claimed is:

1. A supported catalyst comprising:
   (a) a catalyst precursor, wherein the catalyst precursor comprises at least one aromatic group and at least one active catalytic metal, wherein the at least one catalytic metal is selected from the group of Group 3-10 metals of the Periodic Table; and
   (b) a support material, wherein the support material comprises one or more oligomers having 10 mol % to 11 mol % of a terminal unsaturated group, wherein the one or more oligomers do not comprise either an aromatic group or a heteroatom and wherein the catalyst precursor contacts the support material in the presence of a Lewis acid by Friedel Crafts alkylation to form a supported catalyst precursor; and
   (c) a co-catalyst, wherein the co-catalyst contacts the supported catalyst precursor to form the supported catalyst.

2. The supported catalyst of claim 1, wherein the one or more oligomers are selected from the group consisting of linear and branched oligomers.

3. The supported catalyst of claim 1, wherein the terminal unsaturated group is a terminal vinyl group.

4. The supported catalyst of claim 1, wherein the supported catalyst is useful in dimerization, oligomerization or polymerization of addition monomers.

5. The supported catalyst of claim 4, wherein the supported catalyst is useful in dimerization of addition monomers.

6. The supported catalyst of claim 1, wherein the at least one active catalytic metal is selected from the Group 10 metals of the Periodic Table.

7. The supported catalyst of claim 1, wherein the support material is polybutadiene having a molecular weight of between 500 and 500,000, and the terminal unsaturated group is a terminal vinyl group.

8. The supported catalyst of claim 7, wherein the supported catalyst is useful in dimerization, oligomerization or polymerization of addition monomers.

9. The supported catalyst of claim 7, wherein the supported catalysis is useful in dimerization of addition monomers.

10. The supported catalyst of claim 1, wherein the co-catalyst is methylaluminoxane, ethylaluminum dichloride, triethylaluminum, diethylaluminum chloride, tri-isobutylaluminum, or a mixture of any thereof.

11. The supported catalyst of claim 10, wherein the co-catalyst is ethylaluminum dichloride.

12. The supported catalyst of claim 1, wherein the at least one active catalytic metal is nickel.

13. The supported catalyst of claim 1, wherein the one or more oligomers do not comprise a heteroatom selected from the group consisting of sulfur, oxygen, nitrogen and combinations thereof.

14. The supported catalyst of claim 1, wherein the support material is polybutadiene having a molecular weight of about 110,000 and having 10 mol % to 11 mol % terminal vinyl groups.

15. The supported catalyst of claim 1, wherein the support material is polybutadiene having a molecular weight of about 110,000 with 89 mol % to 90 mol % 1,4 linkage of the butadiene monomers and 10 mol % to 11 mol % of the 1,2 linkage of the butadiene monomers.

\* \* \* \* \*